United States Patent [19]
Metz et al.

[11] Patent Number: 5,307,024
[45] Date of Patent: Apr. 26, 1994

[54] LINEARIZED LEVEL-SHIFTING AMPLIFIER

[75] Inventors: Arthur J. Metz, Gervais; James S. Lamb, Portland, both of Oreg.

[73] Assignee: Tektronix, Inc., Wilsonville, Oreg.

[21] Appl. No.: 920,076

[22] Filed: Jul. 27, 1992

[51] Int. Cl.$^5$ .............................................. H03F 3/45
[52] U.S. Cl. ..................................... 330/259; 330/260
[58] Field of Search .................................. 330/69-71, 330/252, 259, 260, 290, 293, 310, 311

[56] References Cited

U.S. PATENT DOCUMENTS 3,622,903 11/1971 Steckler ........................... 330/260 X

*Primary Examiner*—James B. Mullins
*Attorney, Agent, or Firm*—Boulden G. Griffith

[57] ABSTRACT

An all NPN transistor level-shifting differential amplifier has first and second identical amplifier halves, in which each amplifier half includes a passive voltage-shifting network coupled between a load and a current source. A main amplifier has a single-ended voltage input and an output coupled to the first node of the voltage shifting network. An output amplifier has a single-ended current output and an input coupled to the second node of the voltage shifting network. The main amplifier and output amplifiers are coupled together such that a portion of the bias and signal currents flowing through the output amplifier is reused and flows through the main amplifier, reducing bias current and power requirements. The first and second amplifier halves are coupled together with a gain-setting emitter resistor. In addition to reducing the power requirements of the amplifier, the feedback configuration of the level-shifting amplifier also increases linearity over prior art level-shifting amplifiers.

28 Claims, 14 Drawing Sheets

LINEARIZED LEVEL-SHIFTING AMPLIFIER

BACKGROUND OF THE INVENTION

This invention relates generally to differential amplifiers and more particularly to precision linear differential amplifiers with internal level-shifters, allowing fabrication with only NPN bipolar transistors in the signal path.

A prior art level-shifting amplifier 10 is shown in FIG. 1. The differential amplifier 10 can be fabricated in a semiconductor process that has only NPN bipolar transistors, due to the level-shifting networks. Signal carrying PNP transistors are not required. A main differential amplifier includes transistors Q1 and Q2, load current sources I1 and I2, a gain-setting emitter resistor R1, and a differential input formed by single-ended inputs Inputn and Inputp at circuit nodes 12 and 14. The collector of transistor Q2 is coupled to a level-shifting network including capacitor C1 and resistor R4, and to an input and collector node of an output amplified including transistors Q5 and Q6, current sources I5 and I6, and load resistor R5. An identical level-shifting network including capacitor C2 and resistor R2 is coupled to the collector of transistor Q1. An identical output amplifier includes transistors Q3 and Q4, current sources I3 and I4, and load resistor R3. The differential output for amplifier 10 is formed by the single-ended outputs Outn and Outp of each of the output amplifiers at circuit nodes 16 and 18. The level-shifting networks R2, C2 and R4, C1 shown in amplifier 10 of FIG. 1 are commonly known as an "Addis level-shifters." Each level shifter voltage shifts the output of the main differential amplifier down by a voltage equal to I3×R2 and I5×R4, which are normally made to be equal. The output voltage can be shifted down to be equal to or less than the input voltage such that numerous stages can be cascaded together without saturation. The operation of amplifier 10 is further described in U.S. Pat. No. 4,725,790 to Addis, which is hereby incorporated by reference.

The main differential amplifier including transistors Q1 and Q2 can be replaced with a Cascomp amplifier, a cascoded amplifier, or one of several other commonly used configurations. The input signal in each of these amplifier configurations generates a signal current through an emitter coupling resistor R1, which in turn flows through transistors Q1 and Q2. In addition, this signal current flows through transistors Q3-Q6 in the output amplifiers. As a result, sufficient standing current must be maintained by current sources I4, I6, I7, and I8 such that the full signal current dynamic range does not shut off any transistor. Typically, current sources I4 and I6 have a value that is slightly more than twice the value of current sources I7 and I8. The bias currents I4 and I6 are set to equally split the current flowing in transistors Q3-Q4 and Q5-Q6 when no signal is applied. In addition to the large standing current requirement of the differential amplifier 10, the level-shifting networks and configuration of the output amplifiers provide no benefit to the linear accuracy of the main amplifier.

Accordingly, a need remains for an all NPN level-shifting differential amplifier having lower standing current requirements and greater linear accuracy that the prior art amplifier shown in FIG. 1.

SUMMARY OF THE INVENTION

It is, therefore, an object of the invention to provide an all NPN level-shifting amplifier having a low standing current requirement.

Another object of the invention is to improve the linearity of a level-shifting amplifier.

An advantage of the invention is that the benefits of level-shifting, low standing current, and improved linearity are conferred while maintaining high bandwidth.

According to the present invention, an all NPN transistor level-shifting differential amplifier has first and second identical amplifier halves, in which each amplifier half includes a passive voltage-shifting network coupled between a load and a current source. A main amplifier has a single-ended voltage input and an output coupled to the first node of the voltage shifting network. An output amplifier has a single-ended current output and an input coupled to the second node of the voltage shifting network. The main amplifier and output amplifiers are coupled together such that a portion of the bias and signal currents flowing through the output amplifier is reused and flows through the main amplifier, reducing bias current and power requirements. The first and second amplifier halves are coupled together with a gain-setting emitter resistor. In addition to reducing the power requirements of the amplifier, the feedback configuration of the level-shifting amplifier also increases linearity over prior art level-shifting amplifiers.

The foregoing and other objects, features and advantages of the invention will become more readily apparent from the following detailed description of a preferred embodiment of the invention which proceeds with reference to the accompanying drawings.

DETAILED DESCRIPTION

Figure 1:
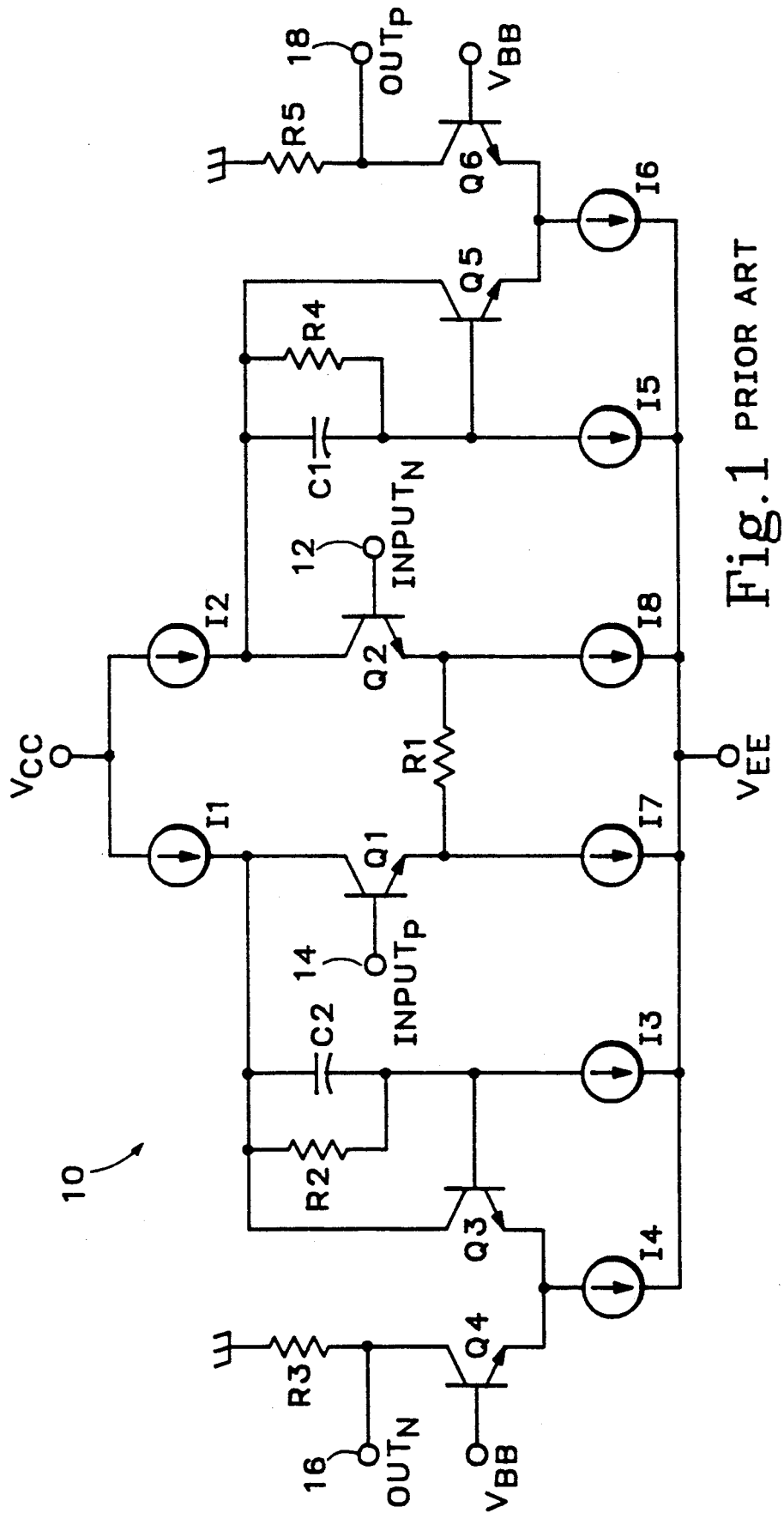
FIG. 1 is a schematic diagram of a prior art all NPN level-shifting amplifier.
Figure 2:
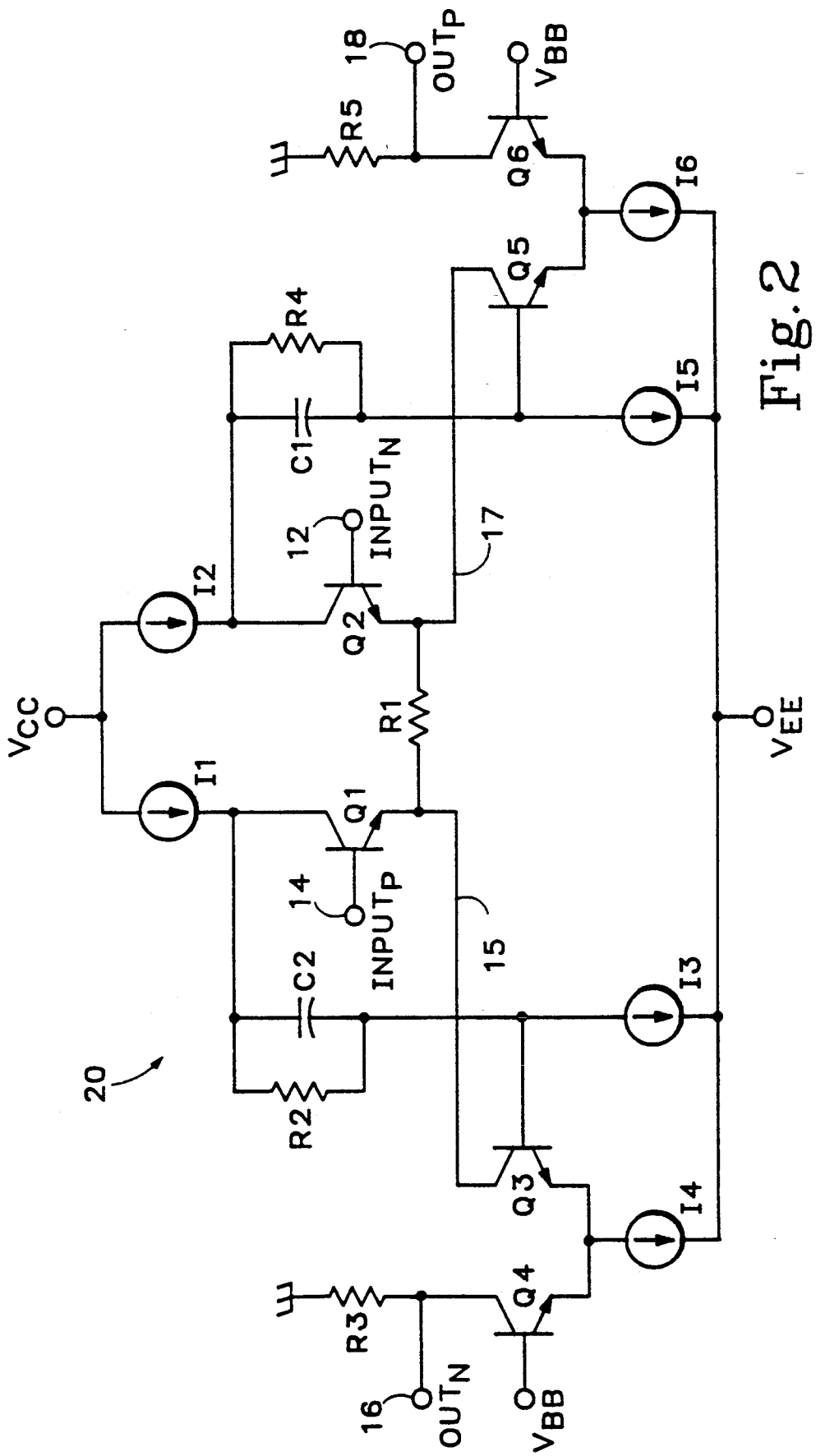
FIGS. 2-13 are schematic diagrams of alternative embodiments of an all NPN level-shifting differential amplifier according to the present invention.

A first embodiment 20 of the level-shifting amplifier of the present invention is shown in FIG. 2. The identification numerals and device labels of FIG. 1 are repeated for the same circuit nodes and devices of FIGS. 2-13. In circuit 20, the collectors of transistors Q3 and Q5 are reconnected to the emitters of transistors Q1 and Q2 through conductors 15 and 17, respectively, instead of to the collectors of transistors Q1 and Q2 in the prior art circuit 10. Note that transistors Q1 and Q2 now supply only the base current drive to the transistors Q3 and Q4, respectively, instead of the collector current drive as in prior art amplifier 10. Thus, nonlinearities caused by the modulation of the emitter current in transistors Q1 and Q2 is greatly reduced. Thermal distortion, consequently, is also greatly reduced. Furthermore, it can be seen that the thermal distortion and nonlinearity of the output pairs (transistor pairs Q3-Q4 and Q5-Q6) is within a feedback loop (Q2-Q5-R4 and Q1-Q3-R2) and thus reduced to a very low level. Also note that the standing current of transistors Q3 and Q5 is reused by transistors Q1 and Q2, eliminating the need for current sources I7 and I8. Current sources I7 and I8 are therefore not used in circuit 20 and the bias current flowing from $V_{CC}$ and $V_{EE}$ is nearly halved.

As in the prior art Addis level-shift amplifier 10, the level-shifter time constants R2×C2 and R4×C1 are set to be approximately equal to the inverse of the transistor rolloff frequency $F_{BETA}$ multiplied by $2\pi$ i.e., $\frac{1}{2}\pi F_{BETA}$. In setting the time constants in this manner, the impedance of the level-shifters can approximate a nearly a constant resistance equal to R2 (or R4) divided by transistor current gain, Beta. The collector voltage of transistors Q1 and Q2 is established by level-shift voltage I3×R2 and I5×R4, respectively, with reference to the bias voltage $V_{BB}$.

As with most feedback amplifiers, the amplifier 20 shown in FIG. 2 requires high frequency compensation to achieve acceptable transient response. One of the more effective ways to accomplish this is with a series R-C network connected from the collector of transistor Q1 (or Q2) to ground, which adds a pole-zero pair to the open loop response. This technique gives good control over the transient response, but usually at the expense of reduced bandwidth.

Figure 3:
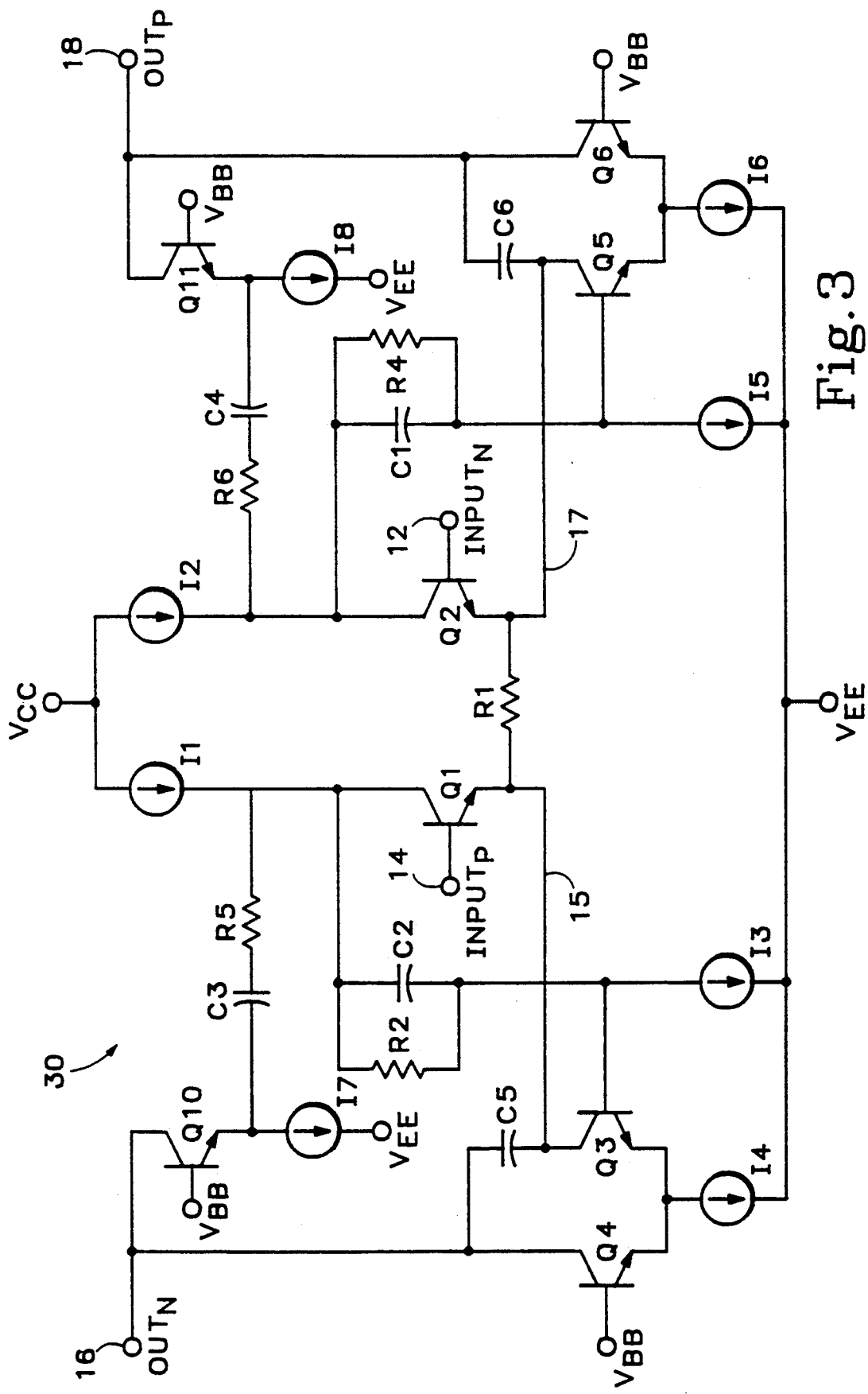

Amplifier 30 shown in FIG. 3 includes series R-C compensation networks R5-C3 and R6-C4 as discussed above, but rather than shunting the compensating current to ground, the current is returned to the output via transistors Q10 and Q11. The series R-C compensation networks are coupled from the collectors of transistors Q1 and Q2 to the emitter of transistors Q10 and Q11, respectively. The bases of transistors Q10 and Q11 are biased to a reference voltage, Vbb, and the emitters of transistors Q10 and Q11 receive bias currents from current sources I7 and I8, respectively. The collectors of transistors Q10 and Q11 are respectively coupled to the output nodes 16 and 18. At higher frequencies, the basic feedback amplifier 10 no longer responds, but transistors Q10, Q11, Q1 and Q2 begin to function as a high bandwidth, Cascode Feed-Beside amplifier, passing input energy directly to the output. The addition of capacitors C5 and C6 to the emitters of transistors Q1 and Q2 results in well controlled front corner peaking of the amplifier step response, with little or no ringing. An additional improvement is realized by connecting the emitter peaking capacitors C5 and C6 directly to the output nodes 16 and 18, causing desirable preshoot in the step response.

Figure 4:
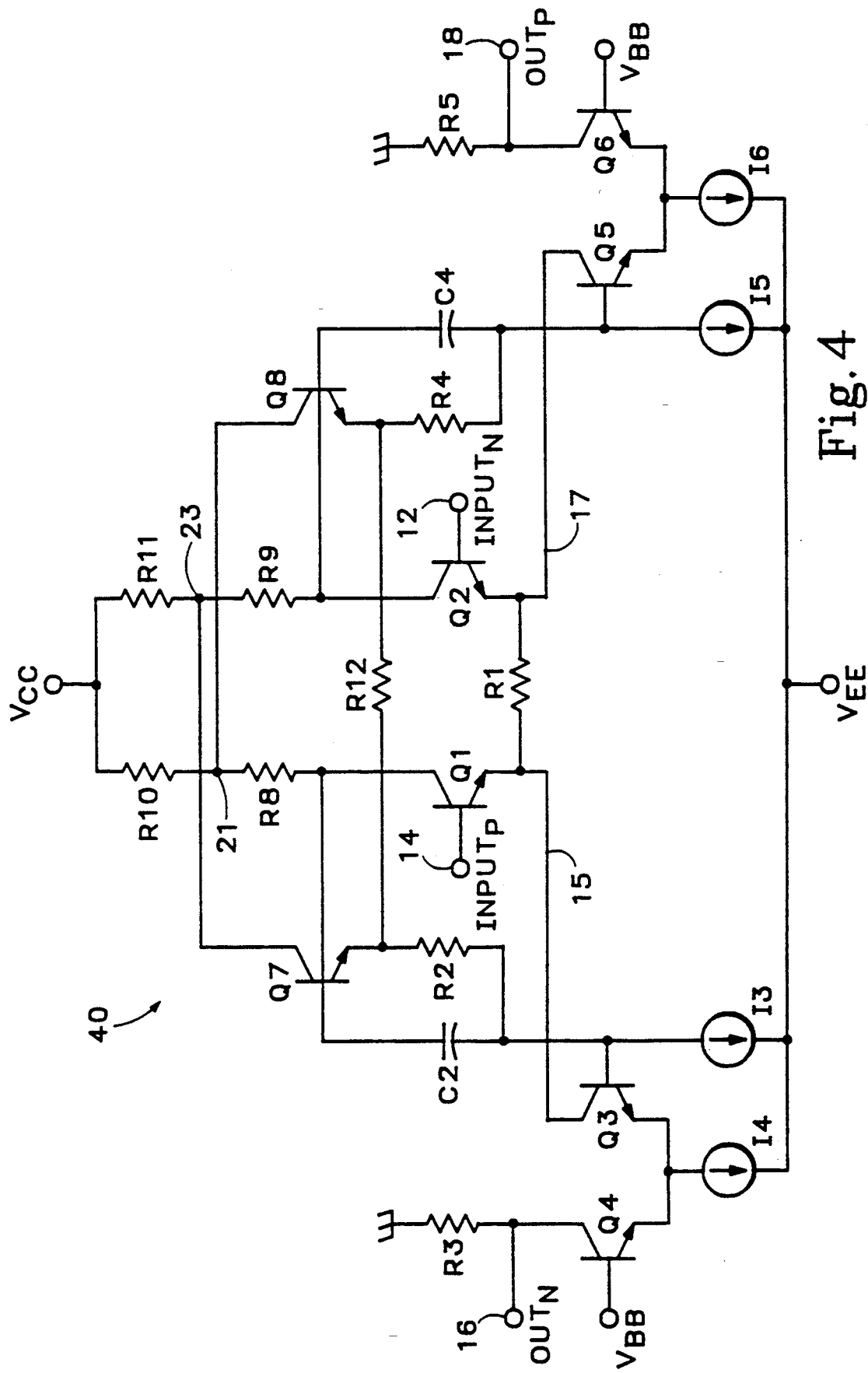

Ideal current sources I1 and I2 can be replaced with PNP transistor current sources if acceptable devices are available or with large value resistors to a high $V_{cc}$ supply voltage. If PNP transistors are not available, or a low $V_{CC}$ supply voltage is used, or if large value load resistors are not feasible, a bootstrapped load can be used to approximate the high impedance of a current source. FIG. 4 shows a bootstrapped amplifier 40 having a bootstrapped resistive current source R8 and R10, which replaces current source I1, and a resistive current source R9 and R11, which replaces current sources I2. The resistive current sources provide a high impedance at the collectors of transistors Q1 and Q2 that keeps the amplifier open loop gain high without using excessive power. Bootstrap transistors Q7 and Q8, in conjunction with emitter-coupling resistor R12 forms a differential pair for injecting signal current into the resistive load. The collector of transistor Q7 is coupled to node 23, which is the junction of resistors R9 and R11, and the base is coupled to the junction of the collector of transistor Q1 and resistor Q8, as well as capacitor C2. The emitter of transistor Q7 is coupled to one end of emitter coupling resistor R12 and resistor R2. Similarly, the collector of transistor Q8 is coupled to node 21, which is the junction of resistors R8 and R10, and the base is coupled to the junction of the collector of transistor Q2 and resistor R9, as well as capacitor C4. The emitter of transistor Q8 is coupled to the other end of emitter coupling resistor R12 and resistor R4.

If resistor R12 is chosen to be equal to the sum of resistor R10 and R11, the resultant voltage across resistors R8 and R9 is held nearly constant. An extremely high equivalent resistance is presented to the collectors of transistors Q1 and Q2. The value of resistors R8 and R9 is nominally set to be equal to the value of resistors R10 and R11. Level-shifting resistors R2 and R4 provide Dc bias current to transistors Q7 and Q8, and capacitors C2 and C4 are respectively coupled to the bases of transistors Q7 and Q8 to avoid the phase shift at the emitters of these transistors. The topology of amplifier 40 provides good AC and DC performance, approximating that of amplifier 20.

Figure 5:
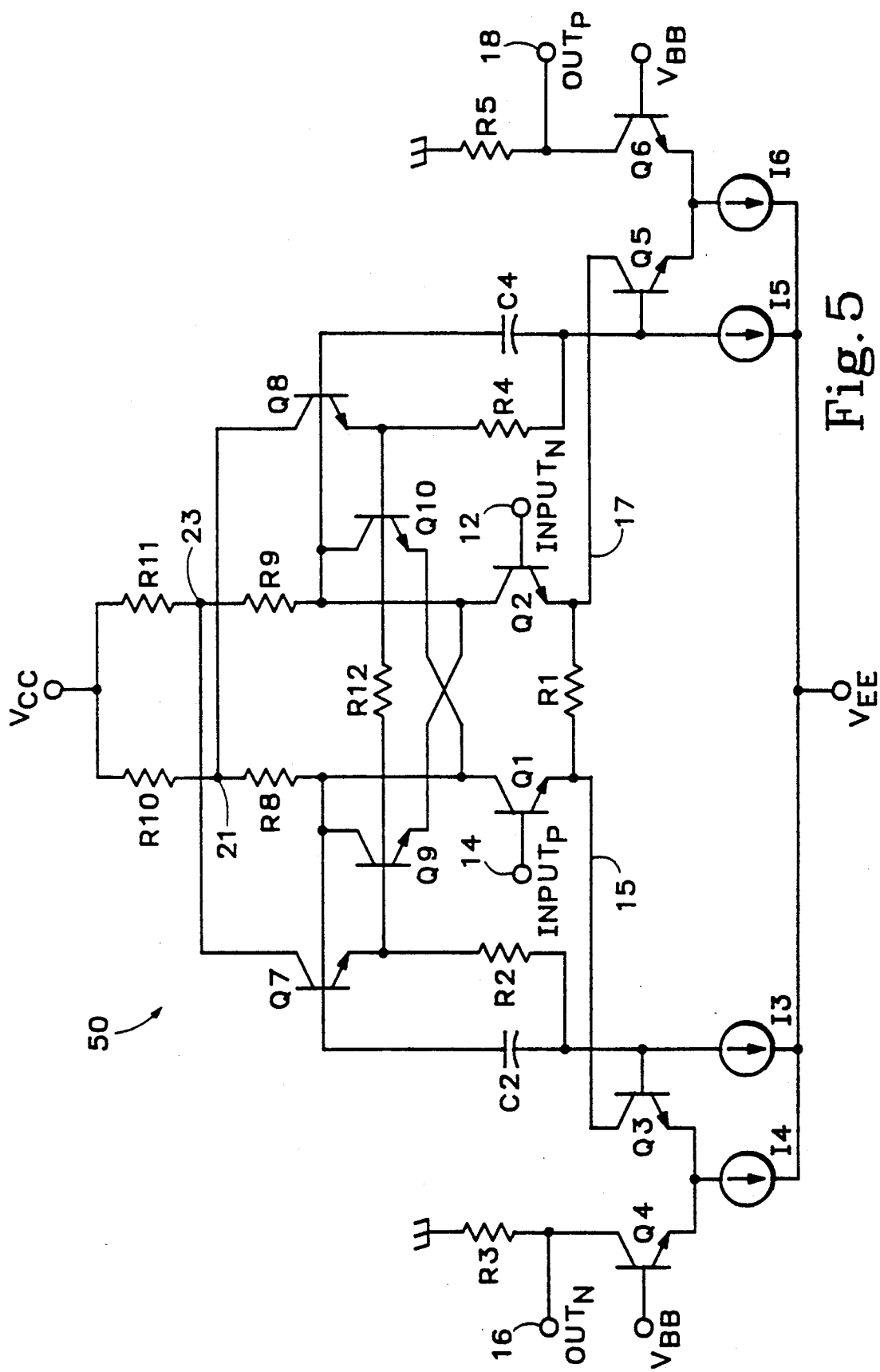

The overdrive performance of the basic amplifier 20 is in fact relatively poor because transistors Q1 and Q5 or Q2 and Q3 can saturate given sufficient input voltage overdrive. An alternative amplifier configuration 50 for a bootstrapped amplifier is shown in FIG. 5 in which clamping transistors Q9 and Q10 are added to the bootstrapped amplifier 40 of FIG. 4 for providing overdrive protection. The base and collector of clamping transistor Q9 are coupled across the base and emitter of transistor Q7. The emitter of clamping transistor Q9 is coupled to the collector of transistor Q2. Similarly, the base and collector of clamping transistor Q10 are coupled across the base and emitter of transistor Q8. The emitter of clamping transistor Q10 is coupled to the collector of transistor Q1.

At the quiescent operating condition, amplifier 50 is biased such that transistor Q4 (Q6) has slightly more standing current than transistor Q3 (Q5). Transistor Q9 and Q10 are off with their emitter-base junctions reversed-biased by the forward-biased emitter-base junctions of transistors Q7 and Q8. As the input voltage increases in a positive direction, the current in resistor R1 increases an equal amount to the reduction in collector current of transistor Q3. The collector current reduction continues until transistor Q3 finally shuts off. Once transistor Q3 is off, the Q1-Q3-Q4 amplifier goes out of regulation, which results in a high impedance at the collector of transistor Q1. A continued increase in input voltage causes a rapid fall in transistor Q1 collector voltage, causing transistor Q10 to conduct, effectively shorting the collectors of transistor Q1 and Q2 together. The output currents of transistors Q4 and Q6 no longer change with a further increase in input voltage, and the transistor Q1-Q2-Q5 loop need only regulate common mode changes in input voltage. Eventually, with sufficient input voltage Q2 shuts off, and the loop is regulated by Q1 and Q5. Essentially, transistors Q9 and Q10 are clamping transistors that turn on during an amplifier overdrive condition. Turning on either transistor Q9 or Q10 ensures that no transistor in amplifier 50 saturates during an overdrive condition and the loop regulation is maintained. Once the overdrive condition is removed, recovery time is at a minimum, and normal operation is restored.

Figure 6:
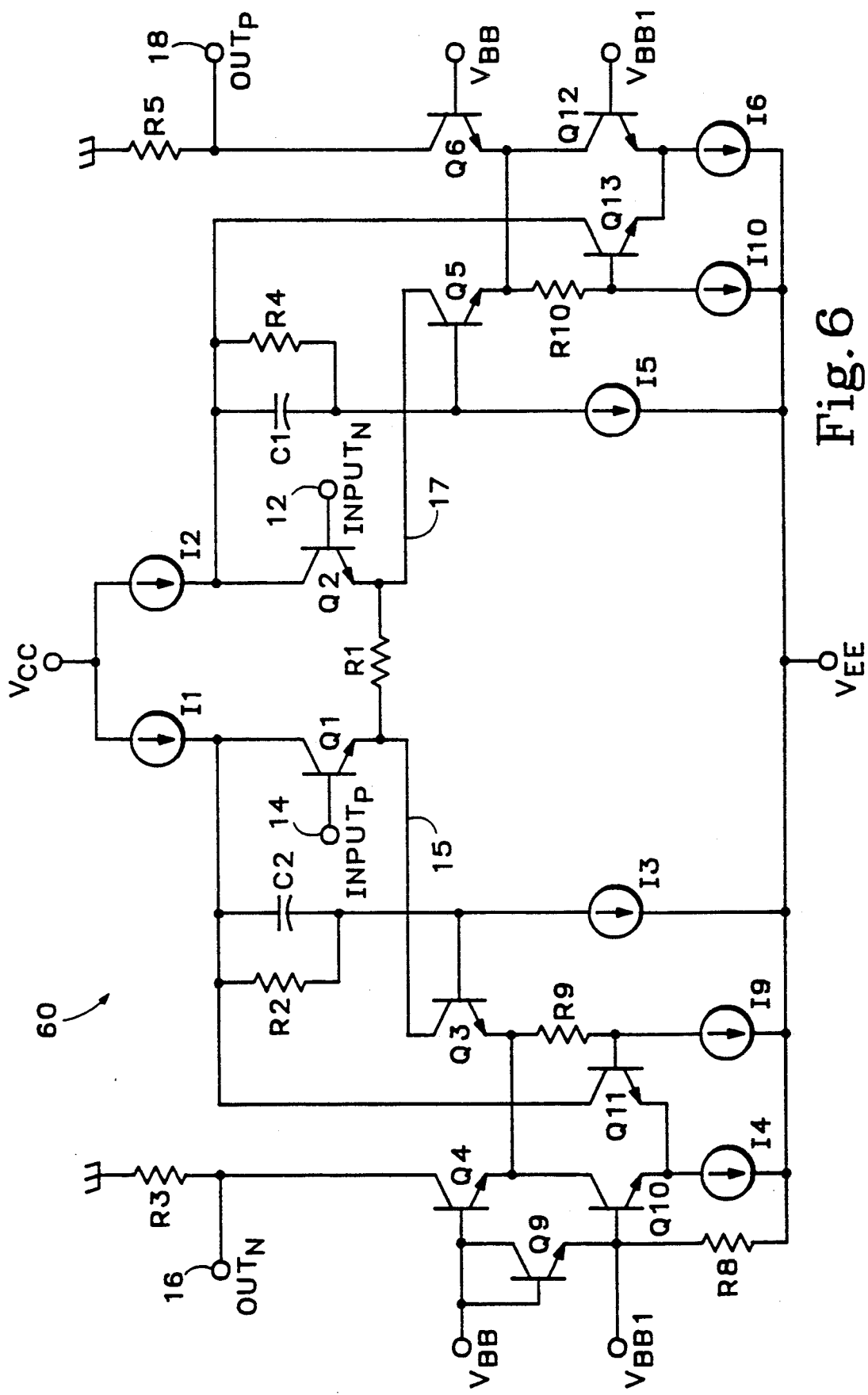

Amplifier 60 shown in FIG. 6 includes an alternative means of clamping amplifier 20 to prevent saturation. Amplifier 60 includes a first differential pair of transistors Q10 and Q11 having an emitter node coupled to current source I4, and a second differential pair of transistors Q12 and Q13 having an emitter node coupled to current source I6. The base of transistor Q10 (Q12) is coupled to a reference voltage Vbb1 and the base of transistor Q11 (Q13) is coupled to one of a resistor R9 (R10), the other end of resistor R9 (R10) being coupled to the emitter of transistor Q3 (Q5). The collector of transistor Q10 (Q12) is coupled to the emitter of transistor Q4 (Q6) and the collector of transistor Q11 (Q13), which provides the clamping current, is coupled to the collector of transistor Q1 (Q2).

Transistors Q11 and Q13 sense the voltage at the emitters of the output transistor pairs. As either transistors Q4 or Q6 begin to turn off, the emitter voltage starts to move positively, which causes the connected clamp transistors Q11 or Q13 to direct current from the bias source to the top of the respective level-shifting network. Essentially, transistors Q10 and Q11 (Q12 and Q13), in conjunction with resistor R9 (R10) and bias voltage Vbb1 form a differential pair for sensing the voltage at the emitters of transistors Q3 and Q4 (Q5 and Q6). Consequently, the loop including the clamp transistor Q11 or Q13 regulates the voltage being applied to the output pair and keeps transistors Q3 or Q5 from being driven into saturation.

Figure 7:
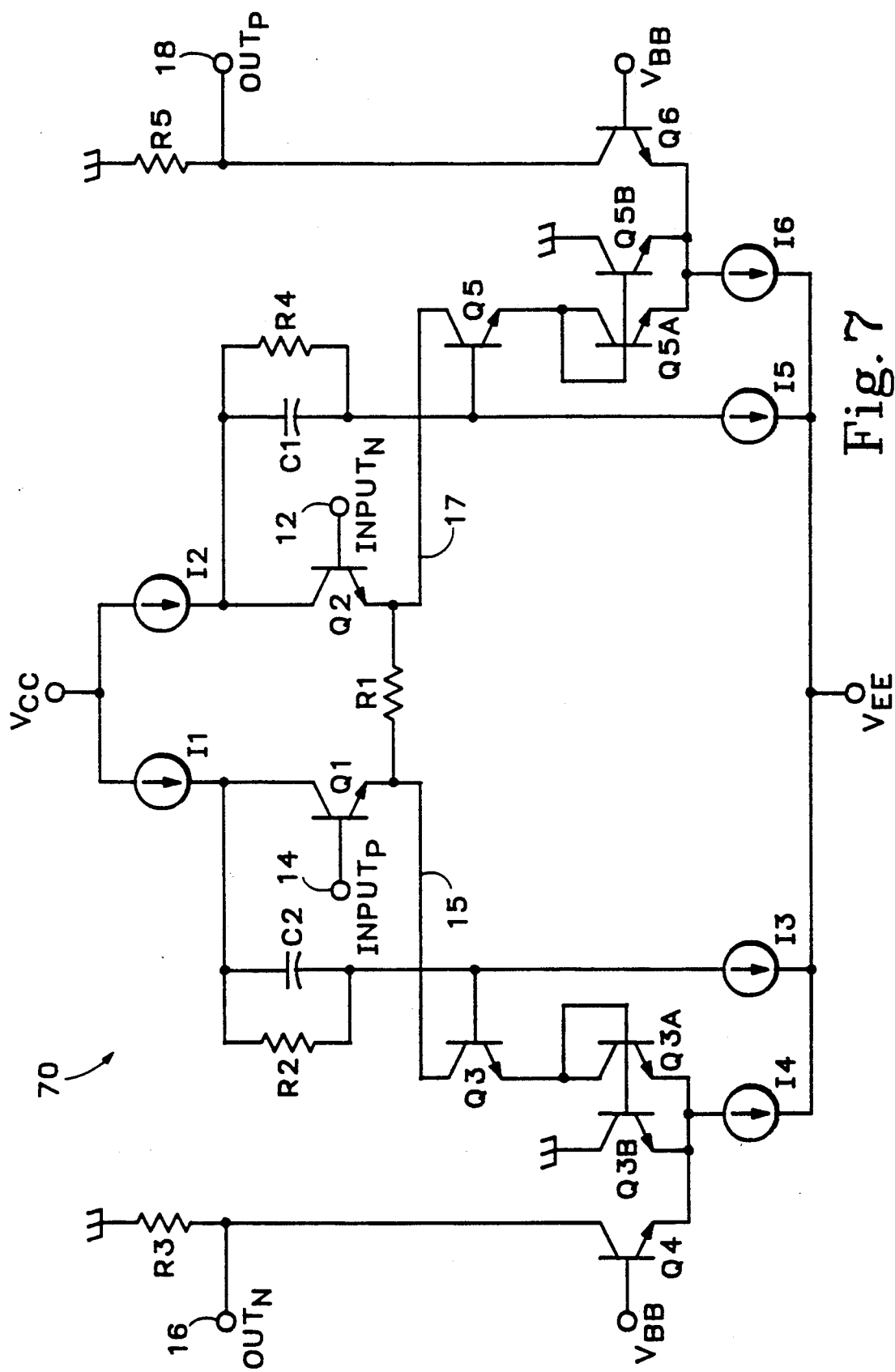

Amplifier 70 shown in FIG. 7 has greater gain-bandwidth (by a factor of two) with higher efficiency than amplifier 20, where efficiency is defined as Isignal/(I1+I2) and Isignal is equal to I(R3)+I(R5). The current from the $V_{CC}$ supply does not contribute to output signal and is wasted. Amplifier 70 includes a three node $F_T$doubler circuit to replace transistors Q3 and Q5. The first $F_T$ doubler circuit includes transistors Q3, Q3A, and Q3B. Transistors Q3A and Q3B are coupled together in a standard current mirror configuration, with the input being the coupled collector and base nodes of transistor Q3A, which is coupled to the emitter of transistor Q3. The collector and base of transistor Q3 forms the collector and base of the $F_T$doubler circuit, whereas the emitter node of the transistor Q3A/Q3B current mirror (which doubles the current) forms the emitter of the $F_T$ doubler circuit. Similarly, a second three node $F_T$ doubler circuit replaces transistor Q5, which includes transistors Q5, Q5A, and Q5B configured in an identical manner.

As taught by Battjes in U.S. Pat. No. 4,236,119, transistors Q3B and Q5B generate signal currents that are nearly equal to those in transistors Q3A and Q5A with little loss of bandwidth. Thus, the output signal current, which flows through the emitter of transistors Q3A and Q3B, is double that which flows through resistor R1 with no increase of $V_{CC}$ supply current and with little loss of bandwidth. Another version of amplifier 70 takes the feedback current from the collector of transistor Q3B (Q5B) instead of transistor Q3 (Q5). Some loss of linearity and increase in thermal distortion results for either of these configurations because transistors Q3A and Q3B (Q5A and Q5B) operate on different load lines.

Figure 8:
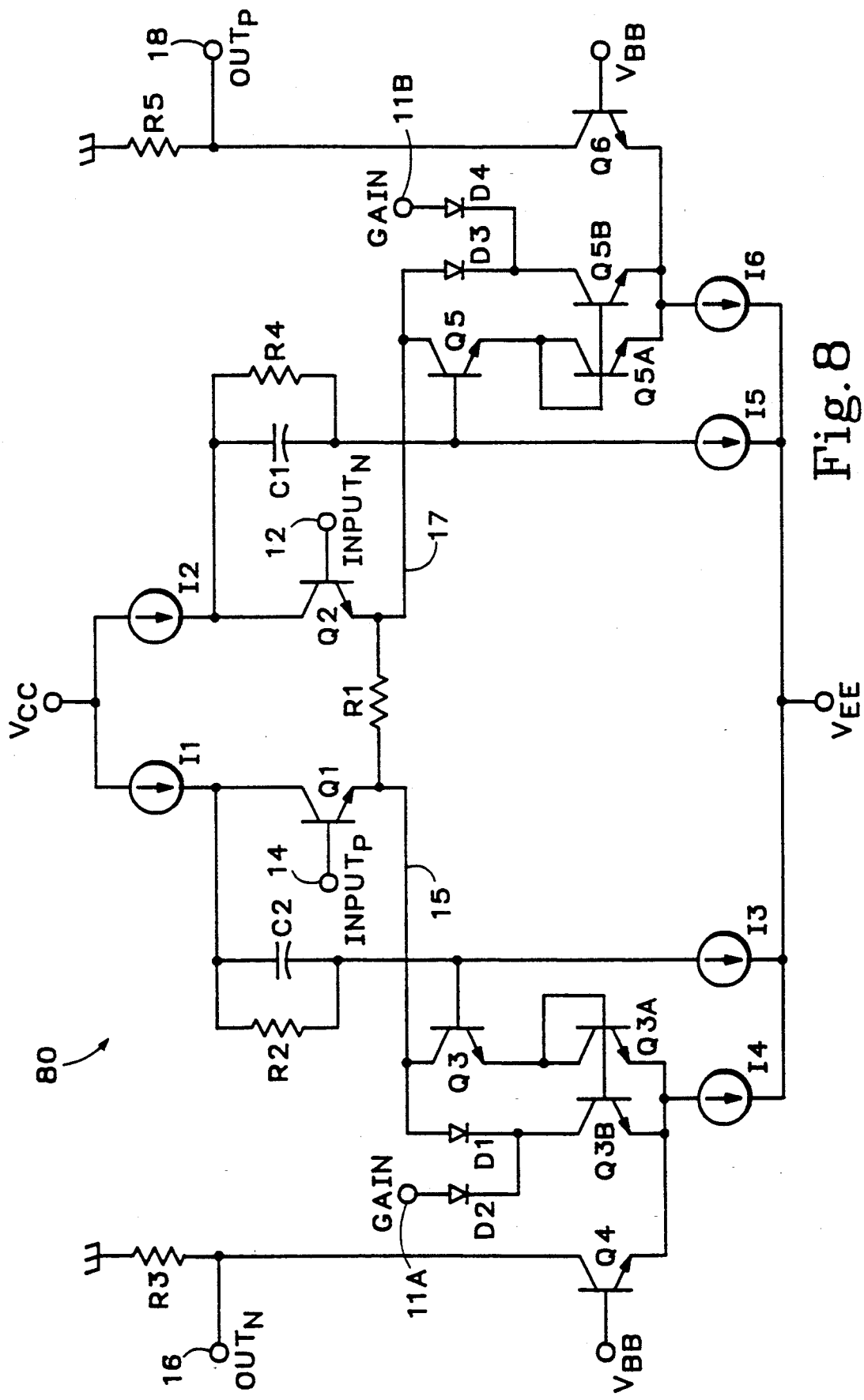

Amplifier 80 shown in FIG. 8 is a variation of amplifier 70, where the addition of diodes D1 through D4 allow the gain to be accurately changed by a factor of two. The ability to change the gain is useful in an oscilloscope, for example, to switch between input attenuator settings without using a relay or separate attenuator circuit. Diodes D2 and D4 have an anode coupled to nodes 11A and 11B for receiving a "GAIN" voltage for changing the gain of amplifier 80. The cathodes of diodes D2 and D4 ar coupled to the collectors of transistors Q3B and Q5B, respectively. Diodes D1 and D3 have an anode coupled to the collectors of transistors Q3 and Q5, respectively, and a cathode coupled to the collector of transistors Q3B and Q5B, respectively.

To increase gain, the voltage at circuit nodes 11A and 11B labelled "GAIN" are pulled sufficiently positive to forward bias diodes D2 and D4 and reverse bias D1 and D3. The collector current of transistors Q3B and Q5B is returned to AC ground, resulting in the factor of two gain improvement over amplifier 20 previously described in conjunction with amplifier 70. When the voltage at the GAIN nodes 11A and 11B is returned low enough to reverse-bias diodes D2 and D4 and forward bias diodes D1 and D3, the collector current of transistors Q3B and Q5B is returned as feedback current, eliminating the doubling action, resulting in the same gain as amplifier 20.

Figure 9:
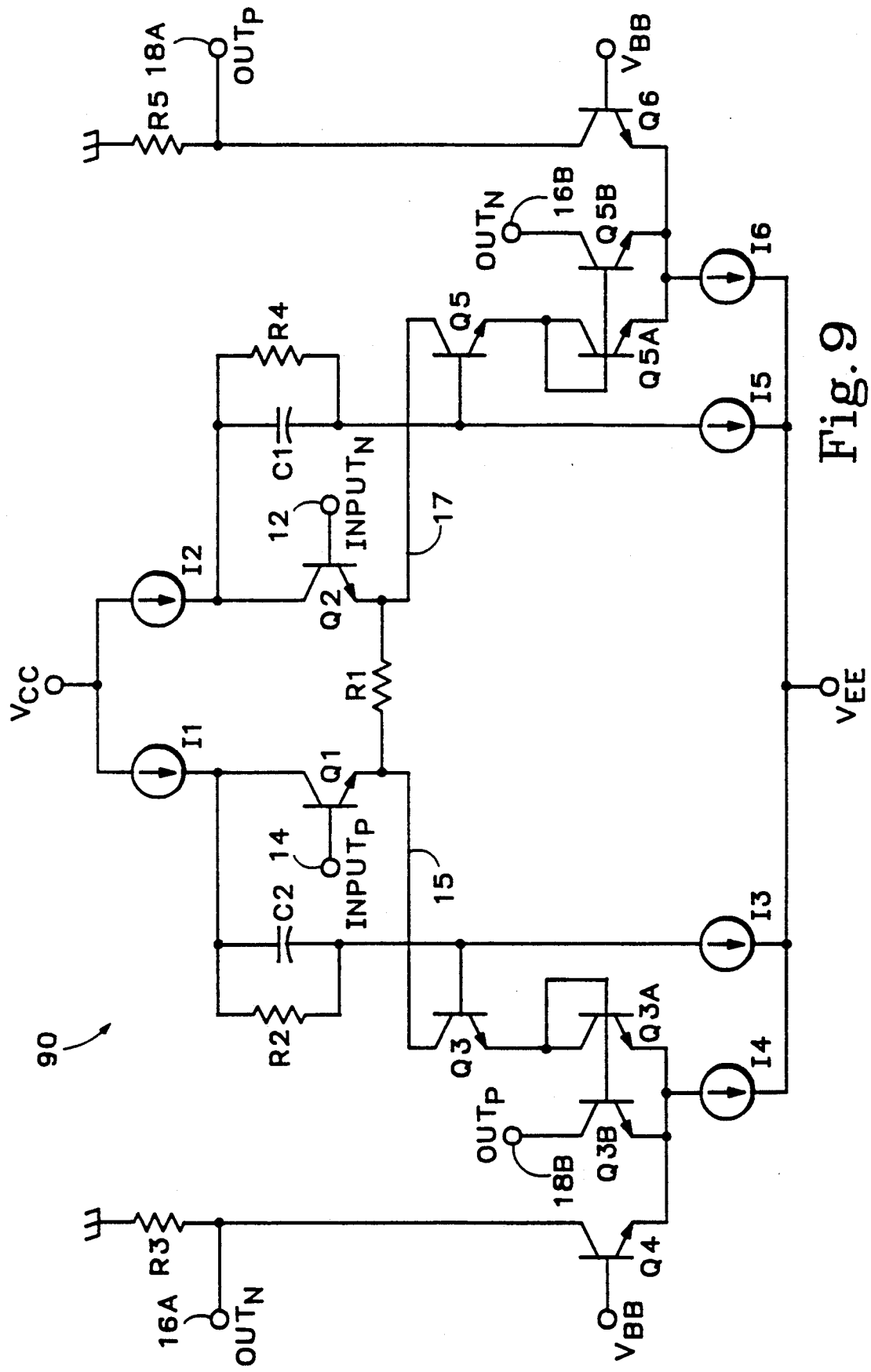

Amplifier 90 shown in FIG. 9 includes a further enhancement that results in the output current being triple that of the basic amplifier 20 with essentially the same bandwidth. While the same component configuration of amplifier 70 is used, the collectors of transistors Q3B and Q5B are coupled to output circuit nodes 18B and 16B, respectively, instead of to ground. The collector currents of transistors Q3B and Q5B, therefore, are delivered to the output of the opposite output pair. Note that the first single-ended output of the amplifier, labeled "Outn" is comprised of circuit nodes 16A, as in amplifier 70, and 16B, the collector of transistor Q5B, which is different than amplifier 70. Similarly, the second single-ended output of the amplifier, labeled "Outp" is comprised of circuit nodes 18A and 18B, the collector of transistor Q3B. There is some increase in distortion compared to the basic amplifier 20, because the mirrored currents in the current mirrors comprised of transistors Q3A/Q3B and transistors Q5A/Q5B are not exactly equal. Note that the collector voltage on each pair of transistors is not equal, which results in errors due to the Early voltage effect.

Figure 10:
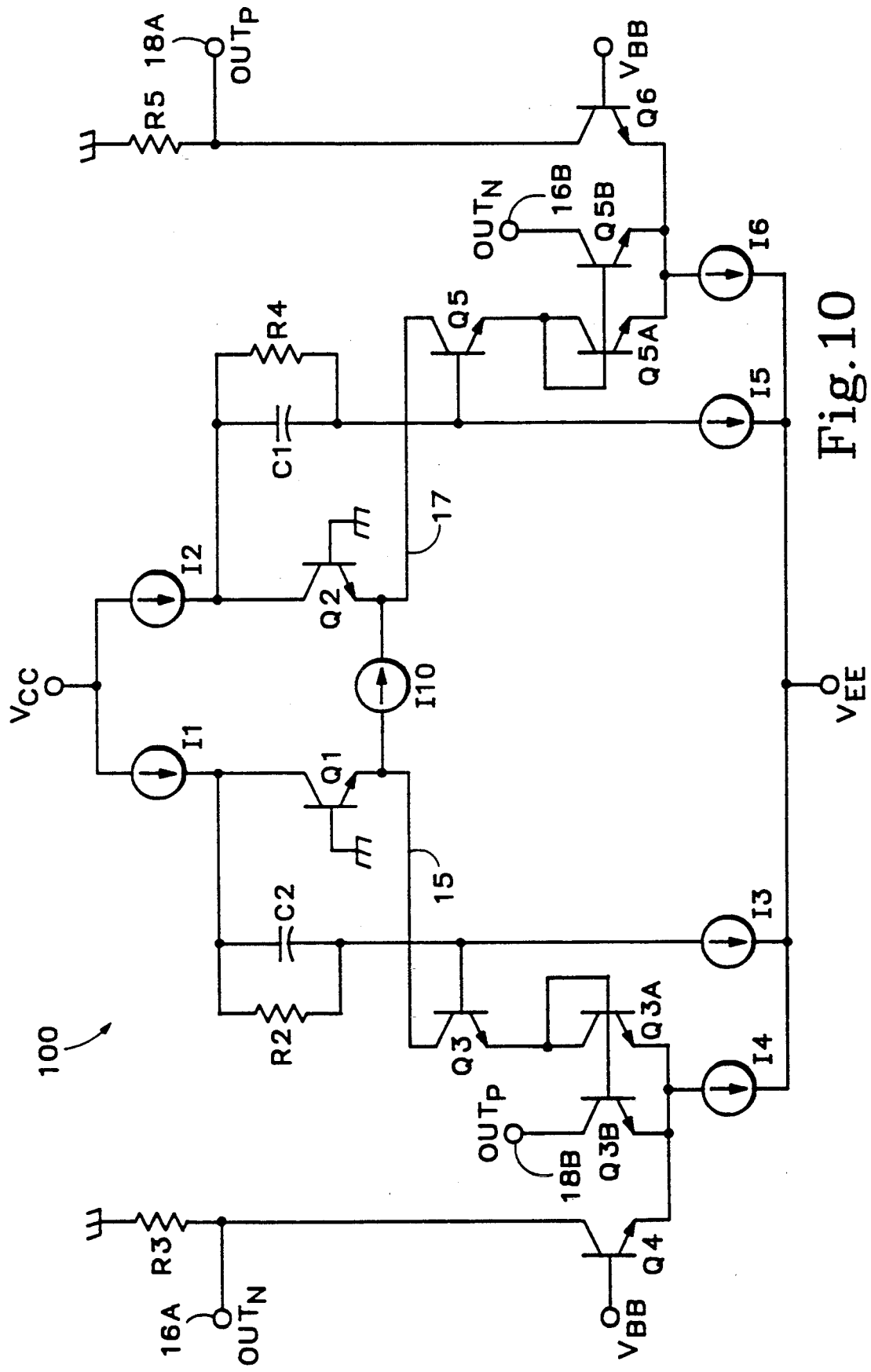

Amplifier 90, which is a transimpedance amplifier, is reconfigured as a current gain amplifier 100 in FIG. 10 (assuming output currents at the collectors of transistors Q4 and Q6). Emitter resistor R1 is removed and replaced by a differential input current I10. The bases of transistors Q1 and Q2 are grounded or tied to a low impedance. The differential input current I10 is driven directly into the emitters of Q1 and Q2. Because of the feedback, the input impedance is a factor of beta (transistor current gain) lower than that of a common base stage. The primary advantage of this configuration is its very high gain-bandwidth product due to the reduction of Miller capacitance on transistors Q1 (Q2) and Q3 (Q4) and the elimination of the input voltage swing at the bases of transistors Q1 and Q2. Thermal distortion is also better because transistors Q1 and Q2 do not contribute thermal errors. The majority of thermal distortion remaining in amplifier 100 is due to load line differences between transistors Q3, Q3B and transistors Q5, Q5B. The bias voltage at the bases of transistors Q1 and Q2 can be used as a thermal adjust voltage to change the power dissipation in transistors Q3 and Q5.

Figures 11, 11B:
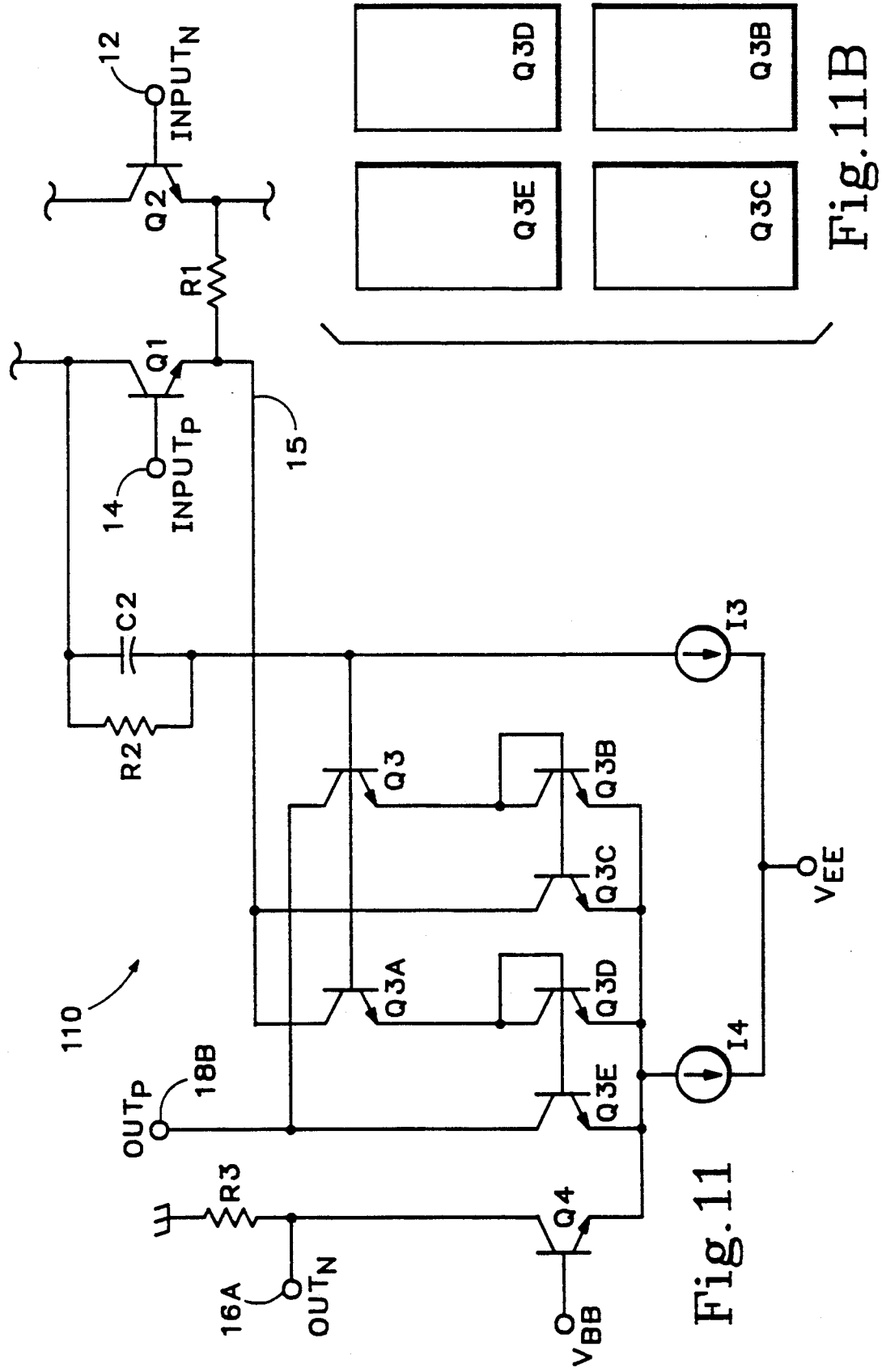
FIG. 11B is a plan view of the layout for a portion of the amplifier shown in FIG. 11.

Amplifier 110, shown in section in FIG. 11, is one of many variations on the $F_T$-doubling amplifier 90. The simple $F_T$-doubling amplifiers including transistors Q3, Q3A, Q3B (Q5, Q5A, Q5B) are replaced with two $F_T$-doubling amplifiers including transistors Q3, Q3B, Q3C and Q3A, Q3D, Q3E. The bases of transistors Q3 and Q3A are coupled together and to one end of the level-shifting network including resistor R2 and capacitor C2. The emitter of transistor Q3 is coupled to the input of a simple current mirror including an input transistor Q3B and an output transistor Q3C. The emitter of transistor Q3A is coupled to the input of a simple current mirror including an input transistor Q3D and an output transistor Q3E. The collectors of transistors Q3 and Q3E are coupled together, and to output node 18B. The collectors of transistors Q3A and Q3C are coupled together and to the emitter of transistor Q1. The emitter nodes of each simple current mirror are coupled together and to the emitter of transistor Q4. Similarly, the simple $F_T$-doubling amplifiers including transistors Q5, Q5A, Q5B are replaced with two $F_T$-doubling amplifier including transistors Q5, Q5B, Q5C and Q5A, Q5D, Q5E in the same configuration (not shown in FIG. 11).

Nonlinearity and thermal distortion are significantly reduced by taking feedback from both diode-connected transistor Q3D and from transistor Q3C, while the output current is comprised of current from diode-connected transistor Q3B and from transistor Q3E. Examining composite transistor Q3, it can be seen that transistors Q3B and Q3D have similar load lines, and Q3C and Q3E have similar operating conditions. This assumes Vout is between ground and $-1V$, giving a first order cancellation of Early voltage induced errors. Further improvements result from quad coupling the Q3B-Q3E transistors through careful layout. A desirable layout of transistors Q3B-Q3E (Q5B-Q5E) on an integrated circuit is shown in plan view in FIG. 11B.

Figure 12:
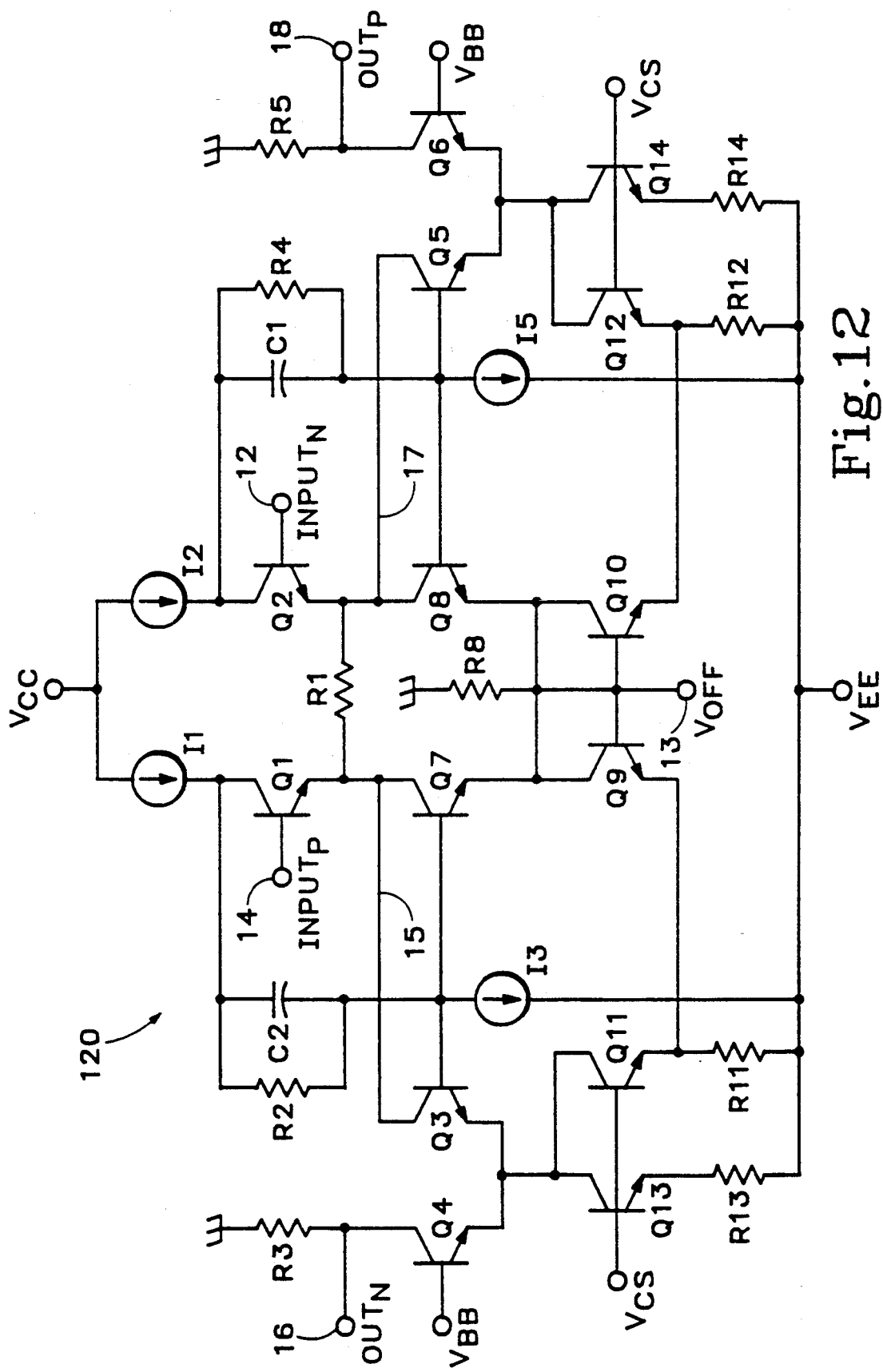

Amplifier 120 shown in FIG. 12 is a variation of the basic amplifier 20 that allows the outputs to be turned off (i.e. decoupled from the input voltage) while maintaining the output common mode voltage, and does so without compromising high frequency response. Amplifier includes an additional differential pair of transistors Q7 and Q8, the collectors of transistors Q7 and Q8 being coupled to the emitters of transistors Q1 and Q2, respectively, and the bases of transistors Q7 and Q8 being coupled to the bases of transistors Q3 and Q5, respectively. An additional resistor R8 is coupled between the coupled emitters of transistors Q7 and Q8 and ground. Diode-connected transistors Q9 and Q10 each have an anode coupled to the emitters of transistors Q7 and Q8, which is also circuit node 13 labeled "Voff". The emitter nodes of the output differential amplifiers are coupled to the collectors of transistors Q11 and Q13, and transistors Q12 and Q14. The bases of transistors Q11-Q14 receive a bias voltage labeled "Vcs". The emitters of transistors Q11-Q14 are coupled to emitter resistors R11-R14, respectively. Additionally, the emitter of transistor Q11 is coupled to the cathode (emitter) of transistor Q9, and the emitter of transistor Q12 is coupled to the cathode (emitter) of transistor Q10.

Normally, the voltage at circuit node 13 is held at a lower potential than the current source bias potential Vcs, such that transistors Q9 and Q10 are not conducting. Resistor R8 pulls the emitters of Q7 and Q8 up to reverse-bias their emitter-base junctions, turning them off as well. As Voff is elevated to Vcs, transistors Q9 and Q10 begin to divert current from transistors Q11 and Q12. The voltage at the bottom of resistor R8 drops until transistors Q7 and Q8 begin to conduct. Eventually, transistors Q3 and Q5 turn off, and all signal current is traded between transistors Q7 and Q8. The total current flowing in the emitters of transistors Q7 and Q8 is constant. As Voff continues to rise, more current flows through resistor R8, dropping the bias voltage at the bases of transistors Q3 (Q5) and Q7 (Q8) reverse-biasing transistor Q3 (Q5) further. The signal path is through transistors Q1, Q2, Q7, Q8, and resistor R1 in the off condition. The current through transistor Q13 (Q14) is chosen to be the same as the quiescent current of transistor Q4 (Q6) so that output common mode voltage is maintained when the outputs are turned off.

Figure 13:
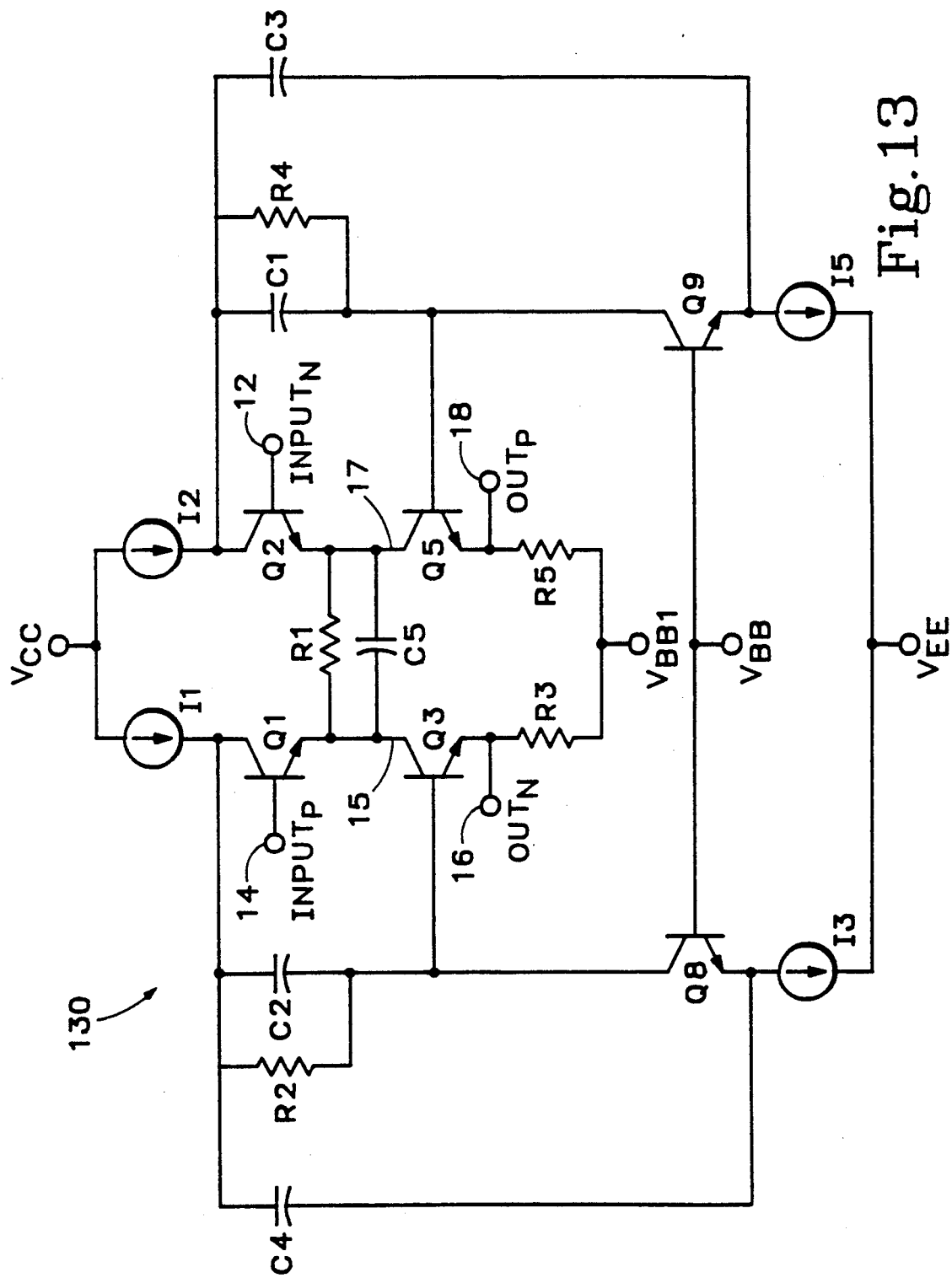

Amplifier 130 shown in FIG. 13 is a derivative of amplifier 20. Amplifier 120 has similar characteristics but offers a means to level-shift to within a few hundred millivolts of the negative rail $V_{EE}$ (as controlled by $V_{BB1}$). Also, power dissipation is lower because the standing current that flowed through Q4 and Q6 is no longer required.

Essentially, in amplifier 130, current sources I4 and I6 are eliminated, and the emitters of transistors Q3 and Q5 are coupled to a reference voltage Vbb1 through load resistors R3 and R4. The reference voltage Vbb1 can be made as low as VEE. The output of amplifier 130 is taken at the emitters of transistors Q3 and Q5. Previous transistors Q4 and Q6 are replaced by transistors Q8 and Q9. The bases of transistors Q8 and Q9 are coupled together and to a second source of reference voltage, VBB. The collector of transistor Q8 (Q9) is coupled to the base of transistor Q3 (Q5) and the level-shifting network R2, C2 (R4, C1). Capacitors C3 and C4 are coupled between the emitter of transistor Q9 and the collector of transistor Q2, and the emitter of transistor Q8 and the collector of transistor Q1, respectively.

Circuit feedback forces an output current at the emitters of transistors Q3 and Q5. The output impedance is therefore established by resistor R3 (R5), and the gain is equal to (R3+R5)/R1 just as it is in amplifier 20. Amplifier 130 has a somewhat reduced bandwidth because of the larger voltage swing at the collectors of transistors Q1 and Q2. The voltage swing at the base of transistors Q3 and Q5 is equal to the output voltage plus $\Delta V_{BE}$ of transistors Q3 and Q5. The larger output voltage increases the effects of parasitic capacitances at these nodes, causing the AC response to begin rolling off at moderate frequencies. Capacitors C3 and C4 are therefore added to couple signal into the current source biased emitters of transistors Q8 and Q9 to compensate for this rolloff. Capacitor C5 may be added in parallel with resistor R1 in order to peak the signal current when driving capacitive loads at the amplifier output.

Figure 15:
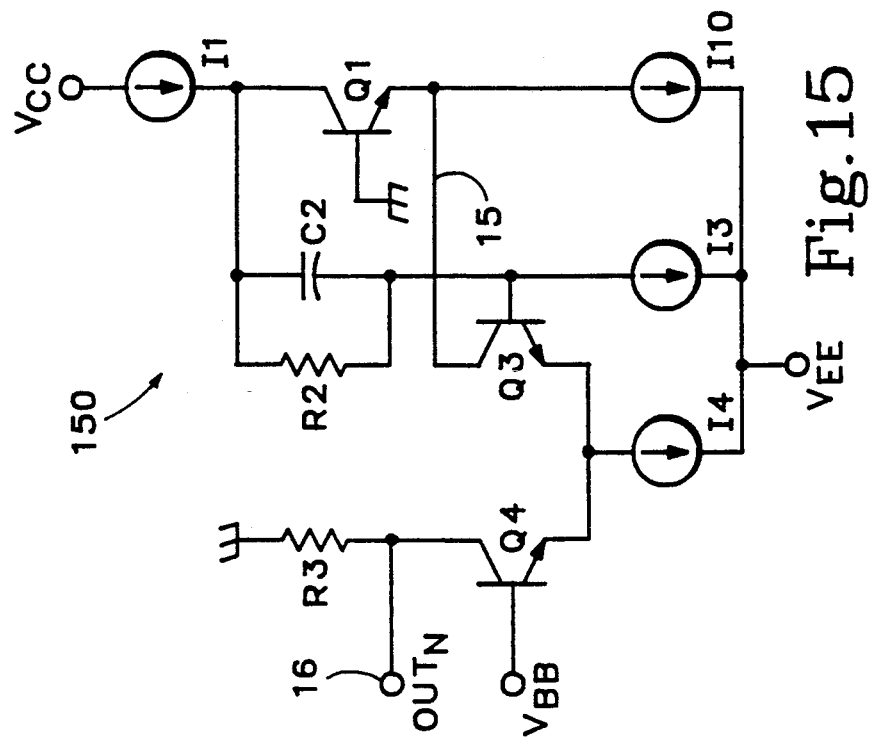
FIGS. 14-15 are schematic diagrams of alternative embodiments of an all NPN level-shifting single-ended amplifier according to the present invention.
Figure 14:
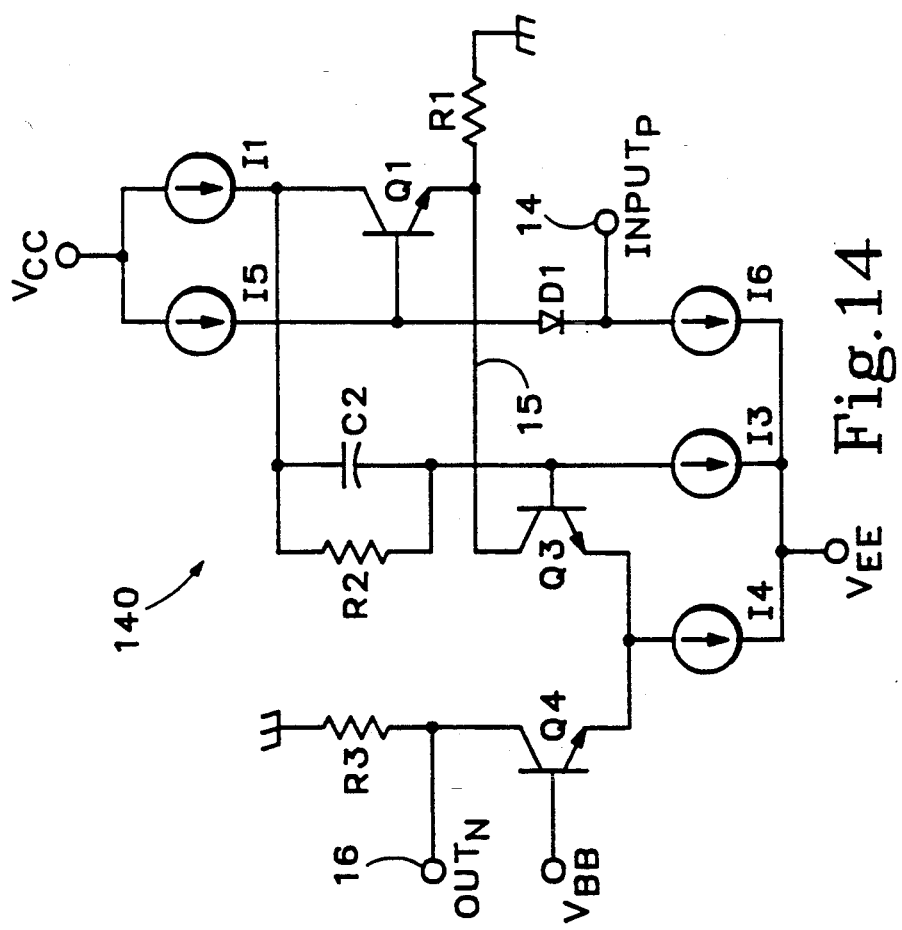

The advantages of linearity, high bandwidth and level-shifting provided by differential amplifiers 20-130 can also be obtained in corresponding single-ended amplifier embodiments. Single-ended embodiments of the present invention are shown in FIGS. 14 and 15. The single-ended embodiment of the present invention is an inverting amplifier that generally corresponds to one amplifier half of the differential amplifiers embodiments 20-130 described above.

Amplifier 140 shown in FIG. 14 is one half of amplifier 20 adapted to receive a single ended voltage input at node 14. The circuit configuration therefore corresponds to one half of the schematic shown in FIG. 2, except for the addition of diode D1 and current sources I5 and I6. These circuit components form an input level-shifting circuit so that the voltage across emitter resistor R1 is nominally zero. Current source I5 is coupled to the base of transistor Q1 and the anode of diode D1.

The cathode of diode D1 is coupled to current source I6, forming voltage input node 14 for receiving the single-ended voltage input. The value of the current supplied by current sources I5 and I6 is desirably set to one half of the value of the current supplied by current source I4. If the currents are set in this manner, the voltage across diode D1 exactly matches the emitter-base voltage of transistor Q1. Since emitter resistor R1 is coupled to ground (or to an appropriate reference voltage), the nominal voltage across resistor R1 is zero. Changes in the input voltage appear directly across resistor R1 without an error component from transistor Q1. It should be noted that the input level shifting circuit I5-I6-D1 is but one of numerous level-shifting circuits that can be constructed to achieve a linear error-free voltage across emitter resistor R1.

Amplifier 150 shown in FIG. 15 is also one half of amplifier 20, but adapted to receive a single-ended current input. The single-ended current source I10 is coupled to the emitter of transistor Q1 and the collector of transistor Q3. Nominally, the value of the current supplied by current source I10 is set to zero. Amplifier 150 is shown as a transimpedance amplifier (voltage output, current input), but is easily configured as a current amplifier (current output, current input) by taking the output current directly at the collector of transistor Q4.

Having described and illustrated the principles of the invention in a preferred embodiment thereof, it is apparent to those skilled in the art that the invention can be modified in arrangement and detail without departing from such principles. We therefore claim all modifications and variation coming within the spirit and scope of the following claims.

We claim:
1. A differential amplifier (20, 30, 40, 50, 60, 70, 80, 90, 110, 120) comprising:
 first and second identical amplifier halves, each amplifier half including
  a load (I1; I2);
  a current source (I3; I4);
  voltage shifting means (R2, C2; R4, C1) having a first node coupled to the load and a second node coupled to the current source;
  a first amplifier (Q1; Q2) having a single-ended voltage input and an output coupled to the first node of the voltage shifting means;
  a second amplifier (Q3, Q4; Q5, Q6) having a single-ended current output and an input coupled to the second node of the voltage shifting means; and
 means (I5, I7) for coupling the first and second amplifiers such that a portion of bias and signal currents flowing through the second amplifier flows through the first amplifier; and
 means (R1) for coupling together the first and second identical amplifier halves, the single-ended voltage input of the first amplifier in each amplifier half forming a differential input, and the single-ended current output of the second amplifier in each amplifier half forming a differential output.

2. A differential amplifier (30) as in claim 1 in which each amplifier half further comprises compensation means (R5, C3, Q10, I7; R6, C4, Q11, I8) coupled between the output of the first amplifier and the single ended current output of the second amplifier.

3. A differential amplifier (40, 50) as in claim 1 further comprising:

an intermediate node (21; 23) in each load (R8, R10; R9, R11); and
bootstrapping means (Q7; Q8; R12) coupled between the first node of the voltage shifting means in each amplifier half and the intermediate node of the load in the opposite amplifier half.

4. A differential amplifier (50) as in claim 3 further comprising clamp means (Q9; Q10) coupled between the first node of the voltage shifting means in each amplifier half and the output of the first amplifier in the opposite amplifier half.

5. A differential amplifier (60) as in claim 1 further comprising clamp means (Q10, Q11, R9, I9; Q12, Q13, R10, I10) in each amplifier half having an input coupled to an emitter node of the second amplifier and an output coupled to the output of the first amplifier.

6. A differential amplifier (70) as in claim 1 further comprising a current mirror (Q3A, Q3B; Q5A, Q5B) in the signal path of the second amplifier of each amplifier half.

7. A differential amplifier (70) as in claim 6 in which an output of the current mirror is coupled to ground.

8. A differential amplifier (80) as in claim 6 further comprising means (D1, D2; D3, D4) for switching the current flow on an output of the current mirror.

9. A differential amplifier (90) as in claim 6 in which an output of the current mirror is coupled to the single-ended current output of the second amplifier in the opposite amplifier half.

10. A differential amplifier (110) as in claim 1 further comprising first and second current mirrors (Q3B, Q3C; Q3D, Q3E; Q5B, Q5C; Q5D, Q5E) in the signal path of the second amplifier of each amplifier half.

11. A differential amplifier (120) as in claim 1 further comprising means (Q7, Q9, Q11, Q13, R11, R13; Q8, Q10, Q12, Q14, R12, R14; R8) coupled between the second node of the voltage shifting means and second amplifier of each amplifier half for decoupling the differential output from the differential input in response to a control signal.

12. A differential amplifier (100) comprising:
 first and second identical amplifier halves, each amplifier half including
  a load (I1; I2);
  a current source (I3; I4);
  voltage shifting means (R2, C2; R4, C1) having a first node coupled to the load and a second node coupled to the current source;
  a first amplifier (Q1; Q2) having a single-ended voltage input coupled to ground and an output coupled to the first node of the voltage shifting means;
  a second amplifier (Q3, Q4; Q5, Q6) having a single-ended current output and an input coupled to the second node of the voltage shifting means; and
 means (I5, I7) for coupling the first and second amplifiers such that a portion of bias and signal currents flowing through the second amplifier flows through the first amplifier; and
 an input current (I10) flowing between the first and second identical amplifier halves and the single-ended current output of the second amplifier in each amplifier half forming a differential output.

13. A differential amplifier (130) comprising:
 first and second identical amplifier halves, each amplifier half including
  a load (I1; I2);

a current source (I3; I4);

voltage shifting means (R2, C2; R4, C1) having a first node coupled to the load and a second node coupled to the current source;

a first amplifier (Q1; Q2) having a single-ended voltage input, and an output coupled to the first node of the voltage shifting means;

a second amplifier (Q3; Q5) having an input coupled to the second node of the voltage shifting means, and a single-ended voltage output; and means (15, 17) for coupling the first and second amplifiers such that a portion of bias and signal currents flowing through the second amplifier flows through the first amplifier; and means (R1) for coupling together the first and second identical amplifier halves, the single-ended voltage input of the first amplifier in each amplifier half forming a differential input, and the single-ended voltage output of the second amplifier in each amplifier half forming a differential output.

14. A differential amplifier (20, 30, 40, 50, 60, 70, 80, 90, 110, 120) comprising:

a main differential amplifier (Q1, Q2, R1) having first and second voltage inputs for receiving a differential input voltage, first and second current outputs, and first and second emitter nodes;

a differential load (I1, I2) coupled to the first and second current outputs;

a first output amplifier (Q3, Q4, I4) having a first voltage input coupled to a source of reference voltage, a second voltage input, a first current output, and a second current output coupled to the first emitter node of the main differential amplifier;

a second output amplifier (Q5, Q6, I6) having a first voltage input coupled to a source of reference voltage, a second voltage input, a first current output, and a second current output coupled to the second emitter node of the main differential amplifier, the first current outputs of the first and second output amplifiers forming a differential current output;

a first level-shifting network (R2, C2) coupled between the first current output of the main differential amplifier and the second voltage input of the first output amplifier;

a second level-shifting network (R4, C1) coupled between the second current output of the main differential amplifier and the second voltage input of the second output amplifier;

a first current source (I3) coupled to the second input of the first output amplifier; and a second current source (I5) coupled to the second input of the second output amplifier.

15. A differential amplifier (30) as in claim 14 further comprising:

first compensation means (R5, C3, Q10, I7) coupled between the first current output of the main amplifier and the second current output of the first output amplifier; and second compensation means (R6, C4, Q11, I8) coupled between the second current output of the main amplifier and the second current output of the second output amplifier.

16. A differential amplifier (40, 50) as in claim 14 in which the load comprises first and second segmented resistors (R8, R10; R9, R11) each having an intermediate node (21; 23).

17. A differential amplifier (40, 50) as in claim 16 further comprising:

a first bootstrapping transistor (Q7) having a base coupled to the first current output of the main differential amplifier, a collector coupled to the intermediate node of the second segmented resistor, and an emitter;

a second bootstrapping transistor (Q8) having a base coupled to the second current output of the main differential amplifier, a collector coupled to the intermediate node of the first segmented resistor, and an emitter;

a resistor (R12) coupled between the emitters of the first and second bootstrapping transistors.

18. A differential amplifier (50) as in claim 17 further comprising:

a first clamp transistor (Q9) having a base coupled to the emitter of the first bootstrapping transistor, a collector coupled to the base of the first bootstrapping transistor, and an emitter coupled to the second current output of the main differential amplifier; and a second clamp transistor (Q10) having a base coupled to the emitter of the second bootstrapping transistor, a collector coupled to the base of the second bootstrapping transistor, and an emitter coupled to the first current output of the main differential amplifier.

19. A differential amplifier (60) as in claim 14 further comprising:

a first clamp circuit (Q10, Q11, R9, I9) having a first input coupled to a source of reference voltage, a second input, a first output coupled to an emitter node of the first output amplifier, and a second output coupled to the first current output of the main differential amplifier;

a first resistor (R9) coupled between the emitter node of the first output amplifier and the second input of the first clamp circuit;

a second clamp circuit (Q12, Q13, R10, I10) having a first input coupled to the source of reference voltage, a second input, a first output coupled to an emitter node of the second output amplifier, and a second output coupled to the second current output of the main differential amplifier;

a second resistor (R10) coupled between the emitter node of the second output amplifier and the second input of the second clamp circuit.

20. A differential amplifier (70) as in claim 14 in which the first and second output amplifiers each comprise:

a first transistor (Q4; Q6) having a base forming the first voltage input, a collector forming the first current output, and an emitter;

a second transistor (Q3; Q5) having a base forming second voltage input, a collector forming the second current output, and an emitter;

a current mirror (Q3A, Q3B; Q5A, Q5B) having an input coupled to the emitter of the second transistor, an output coupled to ground, and an emitter node coupled to the emitter of the first transistor; and a bias current source (I4; I6) coupled to the emitter of the first transistor.

21. A differential amplifier (80) as in claim 14 in which the first and second output amplifiers each comprise:

a first transistor (Q4; Q6) having a base forming the first voltage input, a collector forming the first current output, and an emitter;

a second transistor (Q3; Q5) having a base forming second voltage input, a collector forming the second current output, and an emitter;

a current mirror (Q3A, Q3B; Q5A, Q5B) having an input coupled to the emitter of the second transistor, an output, and an emitter node coupled to the emitter of the first transistor;

a bias current source (I4; I6) coupled to the emitter of the first transistor;

a first diode (D1; D3) having an anode coupled between the collector of the second transistor and the output of the current mirror; and a second diode (D2; D4) having an anode for receiving a control signal and a cathode coupled to the output of the current mirror.

22. A differential amplifier (90) as in claim 14 in which the first and second output amplifiers each comprise:

a first transistor (Q4; Q6) having a base forming the first voltage input, a collector forming the first current output, and an emitter;

a second transistor (Q3; Q5) having a base forming second voltage input, a collector forming the second current output, and an emitter;

a current mirror (Q3A, Q3B; Q5A, Q5B) having an input coupled to the emitter of the second transistor, an output, and an emitter node coupled to the emitter of the first transistor; and a bias current source (I4; I6) coupled to the emitter of the first transistor, wherein the outputs of the current mirrors are cross-coupled to the first current outputs of the first and second output amplifiers.

23. A differential amplifier (110) as in claim 14 in which the first and second output amplifiers each comprise:

a first transistor (Q4; Q6) having a base forming the first voltage input, a collector forming the first current output, and an emitter;

a second transistor (Q3; Q5) having a base coupled to the second voltage input, a collector, and an emitter;

a third transistor (Q3A; Q5A) having a base coupled to the second voltage input, a collector coupled to the second current output, and an emitter;

a first current mirror (Q3B, Q3C; Q5B, Q5C) having an input coupled to the emitter of the second transistor, an output coupled to the second current output, and an emitter node coupled to the emitter of the first transistor;

a second current mirror (Q3D, Q3E; Q5D, Q5E) having an input coupled to the emitter of the third transistor, an output, and an emitter node coupled to the emitter of the first transistor; and a bias current source (I4; I6) coupled to the emitter of the first transistor, wherein the collector of the second transistor and the output of the second current mirror are coupled together and cross coupled to the first current outputs of the first and second output amplifiers.

24. A differential amplifier (120) as in claim 14 further comprising a bias circuit (Q7–Q14, R11–R14) having a pair of inputs coupled to the second voltage inputs of the first and second output amplifiers, a pair of inputs coupled to an emitter node of the first and second output amplifiers, and a pair of outputs coupled to the emitter nodes of the main differential amplifier for decoupling the differential current output from the differential input in response to a control signal.

25. A differential amplifier (100) comprising:

a main differential amplifier (Q1, Q2, R1) having first and second voltage inputs coupled to ground, first and second current outputs, and first and second emitter nodes for receiving a differential input current;

a differential load (I1, I2) coupled to the first and second current outputs;

a first output amplifier (Q3, Q4, I4) having a first voltage input coupled to a source of reference voltage, a second voltage input, a first current output, and a second current output coupled to the first emitter node of the main differential amplifier;

a second output amplifier (Q5, Q6, I6) having a first voltage input coupled to a source of reference voltage, a second voltage input, a first current output, and a second current output coupled to the second emitter node of the main differential amplifier, the first current outputs of the first and second output amplifiers forming a differential current output;

a first level-shifting network (R2, C2) coupled between the first current output of the main differential amplifier and the second voltage input of the first output amplifier;

a second level-shifting network (R4, C1) coupled between the second current output of the main differential amplifier and the second voltage input of the second output amplifier;

a first current source (I3) coupled to the second input of the first output amplifier; and a second current source (I5) coupled to the second input of the second output amplifier.

26. A differential amplifier (130) comprising:

a main differential amplifier (Q1, Q2, R1) having first and second voltage inputs for receiving a differential input voltage, first and second current outputs, and first and second emitter nodes;

a differential load (I1, I2) coupled to the first and second current outputs;

a first output amplifier (Q3, Q5, R3, R5) having a first and second voltage inputs, first and second current outputs coupled to the first and second emitter nodes of the main differential amplifier, and first and second emitter nodes forming a differential voltage output;

a second output amplifier (Q8, Q9, I3, I5) having first and second voltage inputs coupled to a source of reference voltage, first and second current outputs coupled to the first and second voltage inputs of the first output amplifier, and first and second emitter nodes;

a first level-shifting network (R2, C2) coupled between the first current output of the main differential amplifier and the first voltage input of the first output amplifier;

a second level-shifting network (R4, C1) coupled between the second current output of the main differential amplifier and the second voltage input of the first output amplifier;

a first current source (I3) coupled to the first emitter node of the second output amplifier; and a second current source (I5) coupled to the second emitter node of the second output amplifier.

27. A differential amplifier (130) as in claim 26 further comprising:
- a first capacitor (C4) coupled between the first current output of the main differential amplifier and the first emitter node of the second output amplifier; and
- a second capacitor (C3) coupled between the second current output of the main differential amplifier and the second emitter node of the second output amplifier.

28. A differential amplifier (130) as in claim 26 further comprising a peaking capacitor (C5) coupled across the emitter nodes of the main differential amplifier.

* * * * *